US012484887B2

(12) United States Patent
Janssens

(10) Patent No.: US 12,484,887 B2
(45) Date of Patent: Dec. 2, 2025

(54) MEDICAL INSTRUMENT FOR TAKING TISSUE SAMPLES IN THE BODY

(71) Applicant: Jacques Philibert Janssens, Hasselt (BE)

(72) Inventor: Jacques Philibert Janssens, Hasselt (BE)

( * ) Notice: Subject to any disclaimer, the term of this patent is extended or adjusted under 35 U.S.C. 154(b) by 868 days.

(21) Appl. No.: 17/765,794

(22) PCT Filed: Sep. 28, 2020

(86) PCT No.: PCT/IB2020/059034
§ 371 (c)(1),
(2) Date: Mar. 31, 2022

(87) PCT Pub. No.: WO2021/064541
PCT Pub. Date: Apr. 8, 2021

(65) Prior Publication Data
US 2022/0338851 A1 Oct. 27, 2022

(30) Foreign Application Priority Data
Oct. 3, 2019 (BE) .................................. 2019/5649

(51) Int. Cl.
*A61B 10/04* (2006.01)
*A61B 10/02* (2006.01)

(52) U.S. Cl.
CPC .......... *A61B 10/04* (2013.01); *A61B 10/0275* (2013.01)

(58) Field of Classification Search
CPC ................ A61B 10/04; A61B 10/0275; A61B 2010/045; A61B 10/0266; A61B 17/3417; A61B 2017/320032; A61B 10/0233
See application file for complete search history.

(56) References Cited

U.S. PATENT DOCUMENTS

| | | | | |
|---|---|---|---|---|
| 6,083,237 A * | 7/2000 | Huitema | ............ | A61B 10/0233 606/180 |
| 2004/0054377 A1* | 3/2004 | Foster | ................ | A61B 17/3421 606/167 |
| 2011/0224577 A1 | 9/2011 | Park | | |
| 2014/0171826 A1 | 6/2014 | Lampropoulos et al. | | |

(Continued)

FOREIGN PATENT DOCUMENTS

| | | |
|---|---|---|
| EP | 2623036 A1 | 8/2013 |
| WO | 2004006789 A1 | 1/2004 |

OTHER PUBLICATIONS

International Search Report & Written Opinion to corresponding PCT Application No. PCT/IB2020/059034 dated Jan. 19, 2021.

*Primary Examiner* — Eric F Winakur
*Assistant Examiner* — Sienna C Pyle
(74) *Attorney, Agent, or Firm* — Dinsmore & Shohl LLP

(57) ABSTRACT

Medical instrument for taking a tissue sample in the body, the instrument includes an inner tube and an outer tube mounted axially slideable over the inner tube. The inner tube possesses a distal end with a cutting spiral and a proximal end to turn the spiral in the tissue to be sampled. The outer tube possesses a distal end with a cutting edge to cut loose the tissue in the spiral by sliding the outer tube over the spiral. Both tubes over at least an overlapping axial length of 30 cm are executed flexibly bendable because over said length the tubes are provided with one or more grooves which extend through the wall of the tubes and which open upon torsion in one direction.

20 Claims, 4 Drawing Sheets

(56) References Cited

U.S. PATENT DOCUMENTS

| | | | | |
|---|---|---|---|---|
| 2014/0276051 | A1 | 9/2014 | Hoffman | |
| 2015/0223788 | A1 * | 8/2015 | Walther | A61B 10/04 600/564 |
| 2015/0297198 | A1 * | 10/2015 | Bierhoff | A61B 5/6857 600/478 |
| 2016/0331878 | A1 | 11/2016 | McGillicuddy et al. | |
| 2019/0175205 | A1 * | 6/2019 | Vetter | A61B 17/320758 |
| 2021/0038202 | A1 * | 2/2021 | Klein | A61B 10/04 |

* cited by examiner

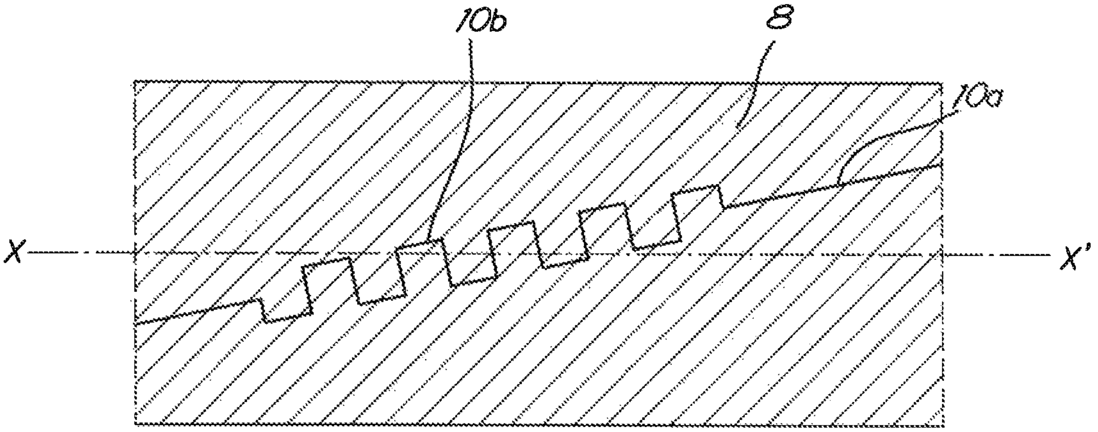
Fig.10
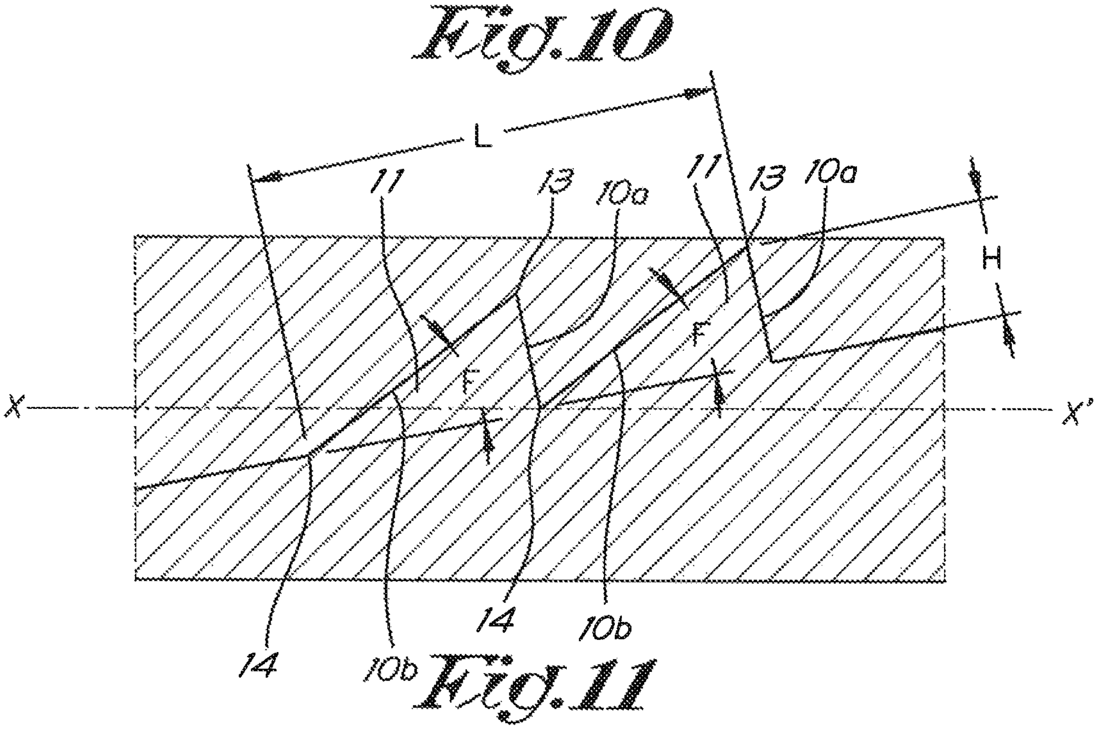
10b Fig.11
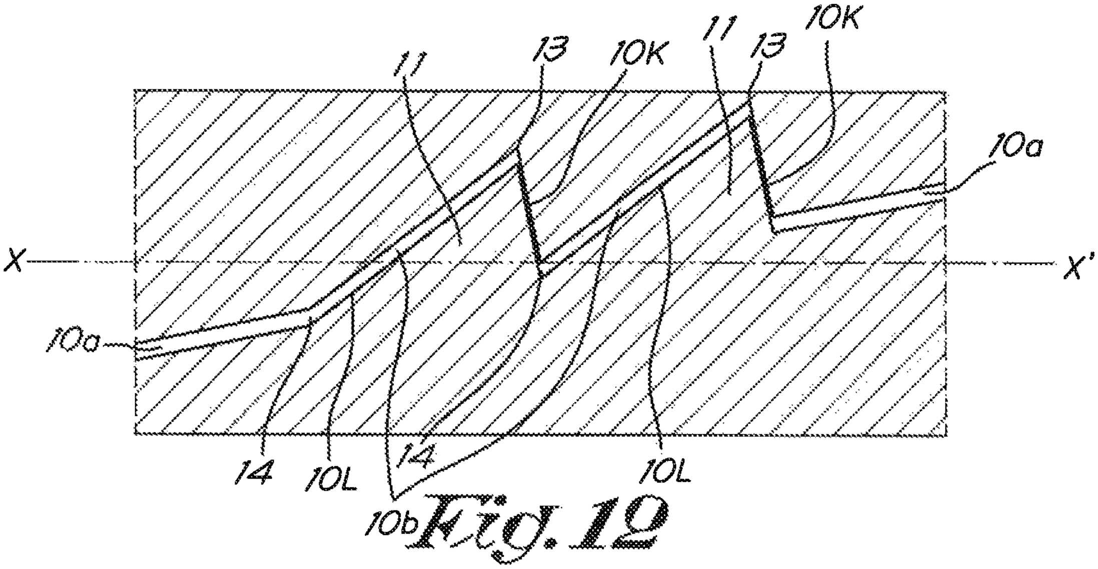
10b Fig.12

MEDICAL INSTRUMENT FOR TAKING TISSUE SAMPLES IN THE BODY

CROSS-REFERENCE TO RELATED APPLICATIONS

The present application is the National Phase entry of International Patent Application No. PCT/IB2020/059034 filed Sep. 28, 2020, which claims priority to Belgium Patent Application No. 2019/5649 filed Oct. 3, 2019, the entire contents of both are hereby incorporated by reference into this application.

TECHNICAL FIELD

The present disclosure relates to a medical instrument for taking a tissue sample in the body.

In particular, the present disclosure is intended for a medical instrument which is composed of at least two tubes which fit into each other, respectively an inner tube and an outer tube which is mounted axially slideable over the inner tube, whereby the inner tube possesses a distal end which in its extension is provided with a cutting spiral and a proximal end to turn the spiral in the tissue to be sampled and the outer tube possesses a distal end with a cutting edge to cut loose the tissue in the spiral by sliding the outer tube over the spiral.

BACKGROUND

When using the instrument the distal end with the tool is inserted via a small incision in the body or via an endoscope to the location needing treatment, while the proximal end sticks out of the body and serves to operate the instrument.

The current instruments are not flexible and the positioning of the tool is via a CT scan or other imaging.

An example of such instrument is described in the EP 2.623.036 of the same inventor for an instrument for taking a tissue sample whereby the instrument is composed of two concentric tubes, respectively an outer tube with a cutting distal end and an inner tube which is rotatably and slideably mounted in the outer tube and which is provided with a spiral-shaped tool which is rotated in the tissue to be sampled. Subsequently, the outer tube is rotated over the spiral-shaped tool to obtain the tissue sample.

Rotating the spiral-shaped tool requires a certain torsional force to penetrate into the tissue.

Another instrument is known from US2016/0331878 with a rigid outer tube and a rigid tube fitting therein, the distal end of which is flexibly executed as a wire-wound spring for aspirating bone marrow via a predrilled hole and for following the form of the bone marrow canal. By rotating the inner tube in a counter direction, the wire windings close to form a canal along which the bone marrow can be aspirated.

The flexible wire-wound end has no penetration capacity to penetrate the tissue such that no high torque is needed at the distal end of the inner tube. Both the outer and the inner tube are rigid with the exception of the wire-wound section which can protrude about five centimetres from the outer tube.

Other applications are also known such as the use of catheters or the like which are flexibly bendable and are inserted by an endoscope which is internally provided with a working channel in which the catheter is slid.

The endoscope itself is also variably flexible over the length and at its distally oriented head is provided with an ultrasound probe such as in US2014/276051 or with lighting and with a digital camera with which the surgeon can examine the location to be treated and can visually follow and lead the actions to be carried out by manipulating the endoscope and the catheter.

Said US2014/276051 talks of a flexible needle of limited length provided with slits to inject a substance which can destroy tissues such as those of a tumour.

US2014171826 and WO2004006789 disclose a medical instrument provided with a penetrating tool at the distal end of an internal tube which is flexible and is slidable arranged within an outer tube. The tool is designed to puncture the tissue to be sampled.

It is a current requirement that, if one wants to use an instrument such as that of the EP 2.623.036 via the internal working channel of a flexible endoscope, said instrument must also have a certain flexibility in terms of bending, specifically must have a greater flexibility than that of the endoscope to not counteract the maximum bend of the endoscope. Moreover, the flexibility must be variable over the length and paired, i.e. in both tubes simultaneously and to the same extent.

The higher the requirements of flexibility are however, the lower the torsional rigidity and in other words the smaller the torsional torque becomes that can be transmitted to the tool and this even more so the smaller the diameter of the instrument that must fit in the working channel is and the longer the length of the working channel.

The internal diameter of the internal channel of the current endoscopes is typically restricted to a few millimetres.

To date, it has not been possible to develop an instrument such as that of EP 2.623.036 which fits in a working channel of said small diameter and which unites a sufficient flexibility with a sufficient torsional rigidity to allow taking a tissue sample. The tissue sample is preferably taken intact (biopsy) unlike aspirate (cytology).

The purpose of the present disclosure is therefore to develop a new medical instrument that does offer this possibility.

SUMMARY

To this end, the present disclosure relates to a medical instrument for taking a tissue sample in the body, whereby the instrument is composed of at least two tubes which fit into each other, respectively an inner tube and an outer tube, the inner tube being slideably and rotatably mounted in the outer tube, whereby the inner tube possesses a distal end which in its extension is provided with a cutting and rotationally penetrating spiral and a proximal end to turn the spiral in the tissue to be sampled and the outer tube possesses a distal end with a cutting edge to cut loose the tissue in the spiral by sliding the outer tube over the spiral, wherein both tubes over at least an overlapping axial length of 30 cm are executed flexibly bendable because over the length the tubes are provided with one or more grooves which extend through the wall of the tubes and which open upon torsion in one direction and thus increase the bendability relative to the resting position without torsion and close upon torsion in the other direction, such that the torsional rigidity is maximal or increases to a maximum with an increasing torsional force for drawing the cutting spiral like a cork screw into the tissue to be sampled upon rotation of the spiral.

Thus the bendability and the torsional rigidity of the tubes can be paired and variably adjusted over the length by a simple rotation in the one or in the other direction, whereby in one direction a greater torsional force can be transmitted to the tool, for example to turn the cutting spiral-shaped biopsy tool of EP 2.623.036 in the tissue, after which the outer tube pushes with its cutting end over the spiral to cut loose the tissue in the spiral and subsequently, by a rotation of the tubes in the other direction, the flexibility can be increased for withdrawing the instrument with the tissue sample from the body.

The use of a cutting spiral for taking a tissue sample is more advantageous than the use of a needle; because on rotation the spiral draws itself into the tissue like a cork screw, less force is needed compared to a needle. Because the spiral draws itself into the tissue the unwanted "push-back" phenomenon of a needle is also avoided whereby the tissue to be sampled is pushed away and the needle is pushed back as a reaction.

Moreover, this technique allows a complete and intact tissue sample to be taken.

The present disclosure is that the instrument must be able to be relatively long with a length of for example one metre or longer and thin with a diameter of, for example 3 mm or less, and despite this must be able to transmit a torque over said length to the spiral-shaped tool to take a sample and still also offer sufficient pressure and tensile resistance.

The flexibility in the overlapping zones of both tubes must be aligned to each other to allow the tubes to be axially slideable and rotatable around their longitudinal axis relative to each other, also when the instrument is bent in curves to guide the cutting spiral to the location of the tissue where the sample is taken, for example via the airways.

In some embodiments, the groove patterns in the overlapping flexible lengths of the tubes are aligned to each other such that in said zones the flexibility of both tubes is equal or practically the same and with a simultaneous rotation also change together.

In this way the flexibility of one tube is not counteracted by the lesser flexibility of the other tube.

In some embodiments, the groove pattern in the overlapping flexible lengths in both tubes is similar or distributed in the same way or even, but not necessarily, practically identical apart from the slight difference in outer diameter.

Consequently, a same flexibility can be obtained as with a spiral spring or with woven wires, but with a greater torque transmission.

In some embodiments, there are two or more parallel primary grooves in every tube which are uniformly distributed over the contour of the tubes and which are axially oriented, which means that in the axial direction they enclose an acute angle which is less than 45°, less than 30°, or less than 15°

Such paired and predominantly axial grooves in the tubes are relatively easy to realise, for example by laser cutting, with which very narrow grooves can also be realised.

The thinner the grooves, the faster they are closed when rotating in one direction and therefore the faster the torsion is built up.

In some embodiments, the width of the grooves is less than a few hundreds of a millimetre or of the order of magnitude of one hundredth of a millimetre.

According to some embodiments, the concerning tubes are manufactured from non-magnetic elastic medical stainless steel. This allows very fine grooves to be realised, for example by laser cutting.

Different forms of paired grooves are possible, each with a specific effect on the bend and torsional rigidity. In this way a distinction can be made between primary grooves which run across the flexible section over longer lengths and can circumferentially go around the tube, the axial vector of which is greater than the circumferential one and secondary grooves which give bulges on the primary grooves. In this way tertiary and subsidiary grooves can also be identified.

A primary groove with a spiral-shaped or sinus-shaped cut with predominantly axial vector in both tubes, will for example allow a flexible bend in both directions with a gradual build up or reduction of the torsional rigidity of the rotation of the tubes in the one or the other direction.

Consequently the pairing of the groove patterns is less critical such that the linear shifting of the tubes relative to each other still allows rotation.

A block-shaped or tooth-shaped secondary cut on the other hand has more of an incremental or discontinuous effect as will appear below.

In some embodiments, the diameter of the outer part of the instrument is less than 2.5 mm or 2 mm at most, such that it can be used in an endoscope with a working channel of said small diameters. The length of both tubes is more than 50 cm.

BRIEF DESCRIPTION OF THE DRAWINGS

With the intention of better showing the characteristics of the present disclosure, a few embodiments of a medical instrument according to the present disclosure for taking tissue samples in the body are described hereinafter by way of an example, without any limiting nature, with reference to the accompanying figures, wherein:

FIG. 10 shows still another variant of FIG. 5 in the resting condition;

FIG. 11 shows still another variant of FIG. 5 in the resting condition; and FIG. 12 shows the section of FIG. 11 under torsional load.

DETAILED DESCRIPTION

Figure 1:
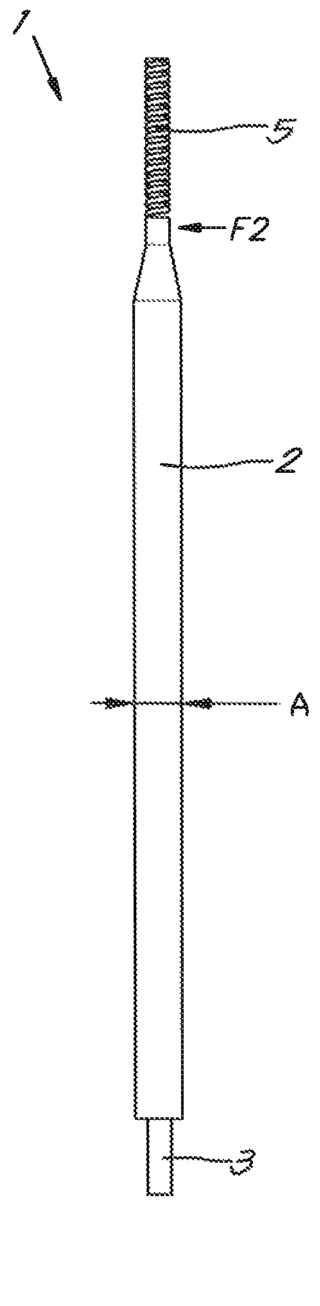
FIG. 1 schematically shows a view of a medical instrument according to the present disclosure.

The instrument 1 of FIG. 1 shown by way of example is an instrument for taking a tissue sample in a patient's body.

The figures are not to scale and are shown out of proportion to better express the dimensional and formal design characteristics.

The instrument 1 is flexibly executed over at least a part C of its length and possesses an outer diameter A which is sufficiently small to be able to fit in a working channel of, for example, less than 2 mm of an endoscope or the like and which must be bendable in curves to, for example, penetrate via the airways into the lungs to locally take a tissue sample there.

The instrument 1 is composed of an outer tube 2 and an inner tube 3 which is slideably and rotatably mounted in the outer tube 2, whereby the outer diameter D of the inner part 3 is slightly smaller than the inner diameter of the outer tube 2 which serves as a kind of sheath for the guidance of the inner tube 3.

In some embodiments, the tubes 2 and 3 are made of a medical stainless steel or another suitable metal.

At the distal end 4 and in the extension thereof, the inner tube 3 is provided with a cutting and rotationally penetrating spiral 5 for taking a tissue sample.

At its proximal end 6 over a certain length B, the inner tube 3 is rigidly executed to form a sort of handle with which the inner tube 3 can be rotated in to turn the spiral 5 around its shaft in the tissue to be sampled and with which the spiral 5 can be held while the outer tube 3 can be axially moved over the spiral to cut loose the tissue that is grabbed by the spiral 5, for which purpose the outer tube is provided with a cutting edge 7 at the distal end. Alternatively the outer tube 2 can be rotated over the spiral 5 to cut off the tissue.

Subsequently, the instrument 1 can be withdrawn from the body to recover the tissue sample.

Figure 2:
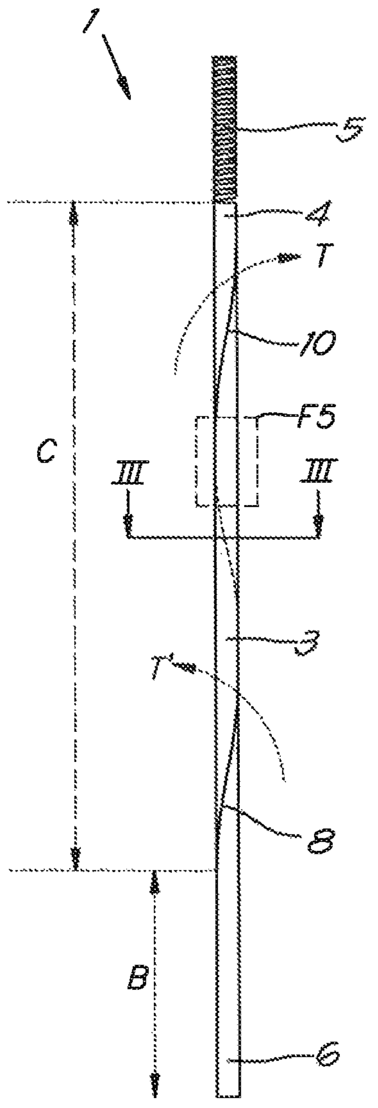
FIG. 2 shows the section of the instrument indicated in FIG. 1 with F2 and this in a resting position.
Figure 3:
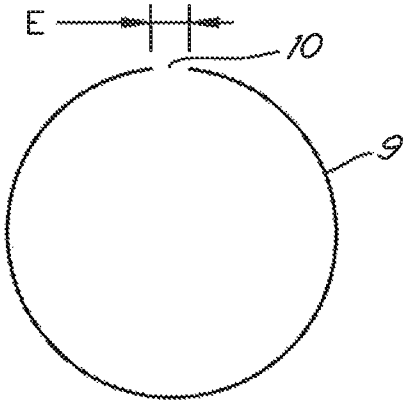
FIG. 3 shows a cross-section according to line III-III in FIG. 2.

The section 8 with length C between the rigid proximal end 6 of the inner tube 3 and the spiral 5 is flexibly executed because in the case of FIG. 2 said section is provided with a cut straight through the wall 9 of the inner tube 3 to form a spiral-shaped or sinus-shaped primary groove 10 which extends along the contour and over the entire length C of the flexible part 8 or over a section of said length C, in this case with one and a half winding. The direction of rotation of the spiral-shaped groove is the reverse to the direction of rotation of the spiral-shaped tool.

The primary groove 10 mostly extends in axial direction, more than in lateral direction, whereby the primary groove in the axial direction X-X' encloses an acute angle S which is less than 45°, less than 30°, or less than 15°.

In some embodiments, the cut is a fine cut with a width E of for example one hundredth of a mm which for example is made with a laser.

The groove 10 forms a device that ensures, when exercising a torsional force T on the proximal end 6 in the opposite direction of rotation of the spiral-shaped groove 10, the groove 10 closes, such that the torsional rigidity increases and is sufficient to turn the spiral-shaped tool 5 into the tissue.

When exercising a torsional force T' in the opposite direction of rotation the groove 10 opens, such that the whole assembly becomes less rigid and the bend flexibility increases, to be able to withdraw the inner tube 3 in the outer tube 2 when the instrument 1 is inserted with one or more curves in the patient's body by an endoscope or the like.

Analogously, the outer tube 2 in the overlapping flexible section 8' is provided with a primary groove 10.

In some embodiments, the grooves 10 in the flexible sections 8 and 8' are aligned such that they result in a similar flexibility of both tubes 2 and 3 in said flexible sections.

Figure 4:
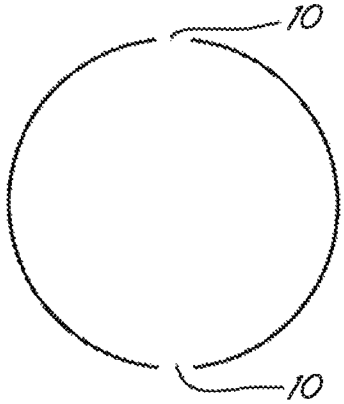
FIG. 4 shows an alternative embodiment according to the cross-section of FIG. 3.

The flexible sections 8, 8' can also be provided with two or more parallel grooves 10 which are uniformly distributed over the contour and thus for example in the case of two grooves 10 are located diametrically opposite each other as shown in FIG. 4 or in the case four grooves 10 are rotated over an angle of 90°. Consequently the flexibility is increased even more relative to one single groove 10.

Figure 5:
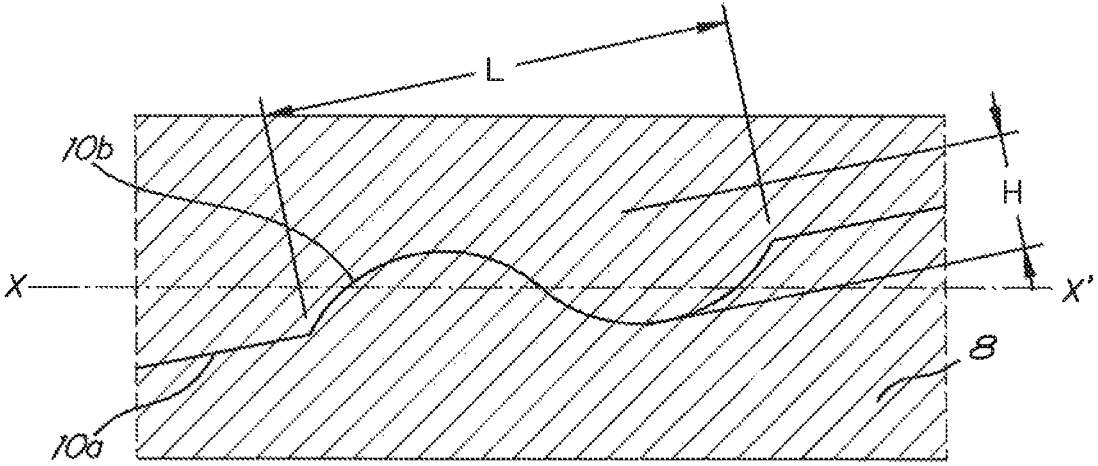
FIG. 5 on a larger scale shows the section indicated in FIG. 2 with the frame F5 but for an alternative embodiment of the present disclosure.

FIG. 5 shows an example of a groove 10 which is composed of a spiral-shaped primary groove 10*a* and a sinus-shaped secondary groove 10*b* grafted thereon formed by a sinus-shaped cut which extends on both sides of the primary cut 10*a*, said sinus showing an amplitude H and extending over an axial length L of the flexible section 8.

When rotating the rigid proximal end 6 in one direction of rotation the cut closes as shown in FIG. 5 while the flexible section 8 becomes longer and thinner with a smaller outer diameter D.

Figure 6:
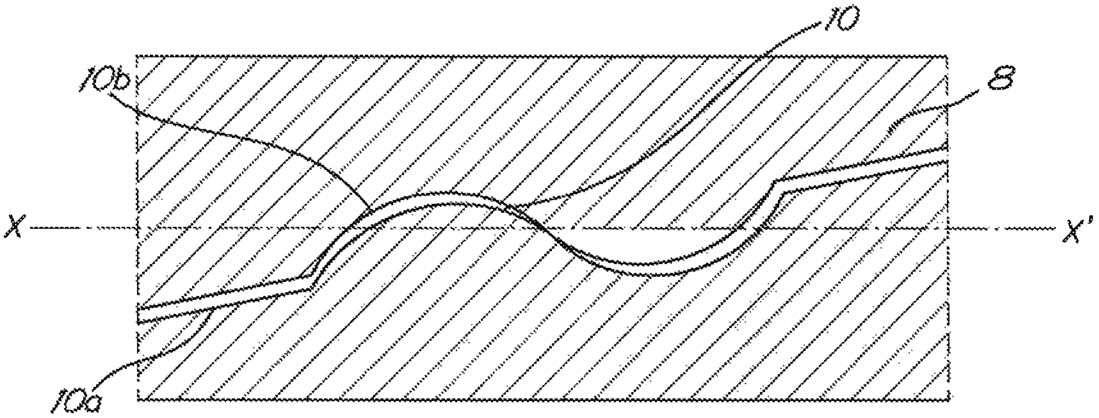
FIG. 6 shows the section of FIG. 5 but in another condition under torsional load, whereby the effect of the torsional load can be observed in the primary and subsidiary grooves.

In case of a rotation in the opposite direction of rotation the groove 10 opens as shown in FIG. 6 (schematically strongly exaggerated).

In FIG. 5, the torsional rigidity and the bend rigidity are maximal, while in FIG. 6 the flexibility has increased.

The sinus-shaped groove 10*b* ensures a flexible bend in both directions of the axis X-X'.

Figure 7:
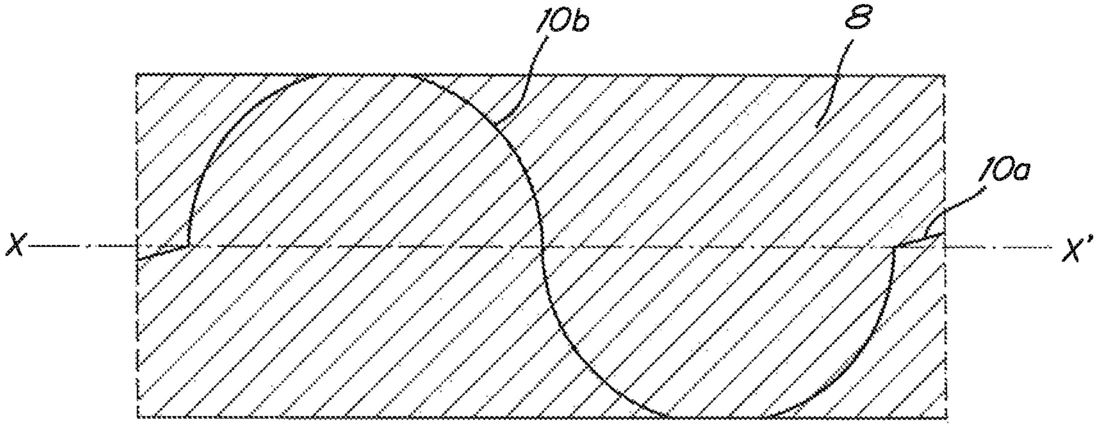
FIG. 7 shows a variant of FIG. 5.

FIG. 7 shows a variant of a sinus-shaped groove 10*b* with a greater amplitude H, whereby the groove 10*b* extends in circumferential direction in this case over a zone that is greater than half the contour of the inner tube 3.

Figure 8:
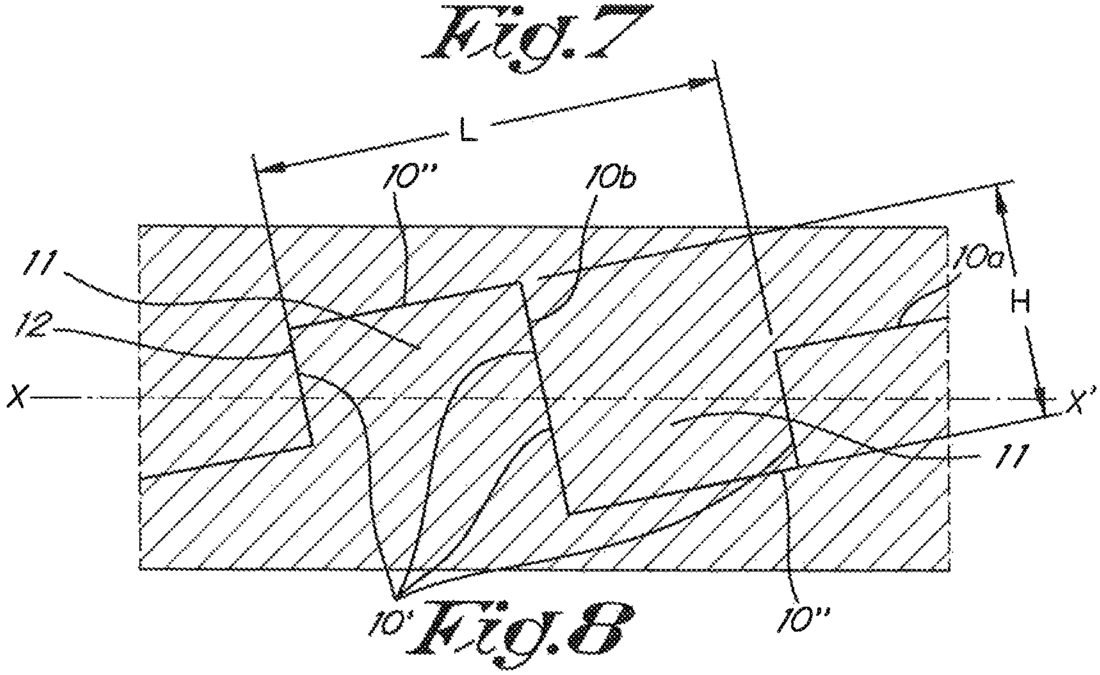
FIG. 8 shows another variant of FIG. 5 in the resting condition.

FIG. 8 shows yet another example of a secondary groove 10*b* which in this case is executed as a block shape and is realised by a cut with U-shaped sections which extend alternatingly on both sides of the primary groove 10*a* with parallel legs 10' which depart from the primary groove 10*a* and extend perpendicularly to said groove 10*a* and which are connected by sections 10" at a distance from the groove 10*a*.

In this way straight block-shaped teeth 11 are cut out as it were which fit in rectangular recesses 12, obtained by the U-shaped cuts 10'-10" in the wall 9 of the tubular inner tube 2.

Figure 9:
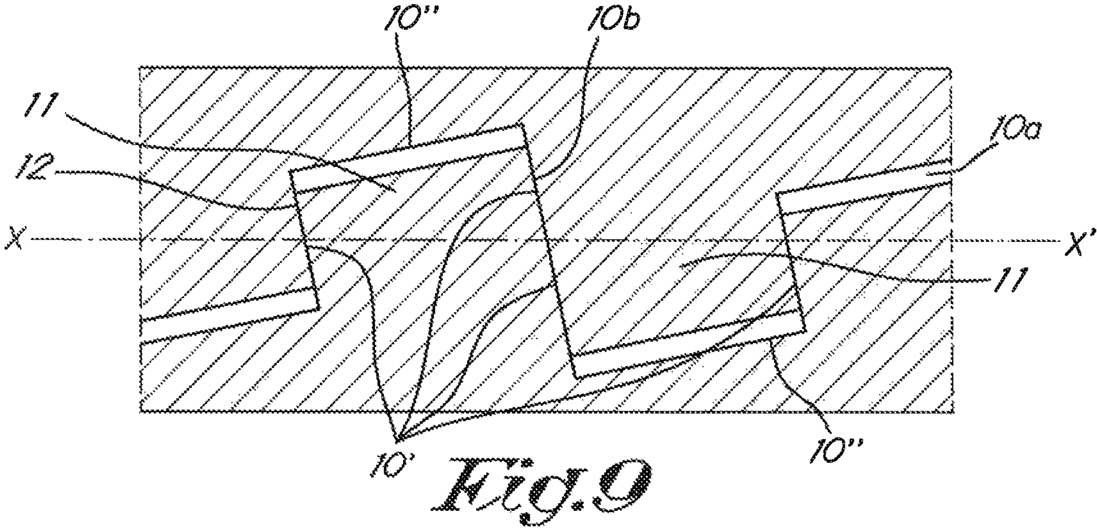
FIG. 9 shows the section of FIG. 8 under torsional load.

In terms of opening and closing upon torsion, the behaviour of the inner tube 3 is analogue as the aforementioned embodiment, whereby FIG. 8 illustrates the condition upon torsion in one direction with closed groove 10 and FIG. 9 shows the condition upon torsion in the other direction with an open groove 10.

FIG. 10 shows an embodiment of a tube with small teeth 11. If the teeth 11 are smaller than the width of the groove 10 when the groove 10 opens a gradual effect can be obtained when the groove 10 opens because the teeth on one side of the line X-X' are than staggered relative to the recesses on the other side of the line X-X'.

In this way the flexibility and the torsional rigidity can also be gradually maintained, also when the torsional force falls away.

Such small toothing 11 can for example also be superimposed on the sinusoidal cut of FIG. 6.

Yet another type of groove is shown in FIG. 11, in which a toothed secondary groove 10*b* is shown which is obtained by a cut with V-shaped sections to form oblique teeth 11 which extend like a sort of sawtooth toothing on one side of a spiral-shaped primary cut 10*a* and whose tip 13 points away from the primary groove 10*a*.

In the example shown of FIG. 11 the V-shaped sections of the groove 10 have a short leg 10K which is perpendicular to the primary groove 10*a* and a long leg 10L which encloses an acute angle F with the primary groove 10*a*.

The groove 10 is continuously cut such that the V-shaped sections with said acute angle F point in the same direction of a same end, for example with the tip 14 in the direction of the end 4 with the spiral 5.

In this case, when exercising a torsion in one direction, the rotation will occur flexibly thanks to the oblique cut formed by the long leg 10L, but in the event of a torsion in the other direction, the rotation will be abruptly blocked by the straight angle of the teeth 11 formed by the short leg 10K engaging with the recesses 12.

Depending on the direction in which the acute angle F is oriented, in the event of a rotation either the transmitted torsional torque at a maximum value will be maintained at a constant fixed and desired value, or the flexibility will be maintained.

Thus, the tool can, for example, be safeguarded from an overload in case of use that could break or damage the tool 5.

The outer tube 2 can also be made from elastic medical stainless steel and will be executed with one or more primary grooves with which the flexibility and the torsional rigidity can be locally influenced by a torsion in the one or other direction simultaneously and paired with the inner tube.

It is also not excluded that the grooves 10 extend over the entire length B of the flexible part 8, but that in this part 8 shorter grooves are applied which, for example overlap each other lengthways or are positioned in a staggered way such that a variable flexion/torsion is possible.

Different types of grooves 10 can also be combined on the same tube 2 or 3. The sort of grooves is also not restricted to the type as described above.

In some embodiments, the grooves 10 are such that both tubes 2 and 3 in overlapping flexible zones yield the same flexibility, because the groove pattern is uniformly distributed or similar or even identical, but laterally shifted in the circumferential direction of the tubes 2 and 3.

The present disclosure is by not limited to the embodiments described as an example and shown in the drawings, but a medical instrument according to the present disclosure for performing a medical procedure in the body can be realised in all kinds of forms and dimensions, without departing from the scope of the present disclosure.

The invention claimed is:

1. A medical instrument for taking a tissue sample in the body, the instrument comprising:

an outer tube; and an inner tube being slideably and rotatably mounted in the outer tube, wherein the inner tube possesses a distal end which in its extension is provided with a cutting and rotationally penetrating spiral and a proximal end to turn the spiral in the tissue to be sampled, wherein the outer tube possesses a distal end with a cutting edge to cut loose the tissue in the spiral by sliding the outer tube over the spiral, wherein the outer tube and the inner tube include a flexible portion over at least an overlapping axial length of 30 cm, the flexible portion having a groove pattern with one or more grooves which extend through a wall of the outer tube and a wall of the inner tube and which open upon torsion in a first direction and thus increase a bendability relative to a resting position without torsion and close upon torsion in a second direction opposite the first direction, such that a torsional rigidity is maximal or increases to a maximum with an increasing torsional force for drawing the cutting spiral like a cork screw into the tissue to be sampled upon rotation of the spiral.

2. The medical instrument according to claim 1, wherein the overlapping flexible lengths of the groove pattern in the outer tube and the inner tube is such that in the lengths the flexibility of the outer tube and the inner tube is equal.

3. The medical instrument according to claim 1, wherein the groove pattern in the outer tube and the inner tube is similar along the overlapping flexible lengths.

4. The medical instrument according to claim 1, wherein there are two or more parallel primary grooves which are uniformly distributed over a contour of the outer tube and the inner tube and which in an axial direction enclose an acute angle which is less than 45°.

5. The medical instrument according to claim 1, wherein the outer tube and the inner tube include a rigid section without the grooves at the proximal end of the instrument.

6. The medical instrument according to claim 1, wherein the outer tube and the inner tube are provided with at least one spiral-shaped primary groove which extends in one or more windings or a section of a winding along the contour of the outer tube and the inner tube.

7. The medical instrument according to claim 1, wherein the outer tube and the inner tube are provided with at least one groove which is composed of a primary longitudinal groove and secondary grooves grafted thereon which extend on both sides of the primary groove.

8. The medical instrument according to claim 6, wherein the outer tube and the inner tube are provided with at least one primary groove which is spiral-shaped and runs over equal lengths and with the same pitch in the outer tube and the inner tube.

9. The medical instrument according to claim 7, wherein the outer tube and the inner tube contain one or more sinus-shaped secondary grooves which extend alternatingly on both sides of a primary groove in overlapping lengths of the outer tube and the inner tube.

10. The medical instrument according to claim 7, wherein at least one secondary groove is a block-shaped groove which extends alternatingly on both sides of a primary groove with sections departing from the primary groove perpendicular to the primary groove and which are connected by sections at a distance from the primary groove in both the outer tube and the inner tube.

11. The medical instrument according to claim 7, wherein the outer tube and the inner tube contain one or more toothed secondary grooves in the overlapping lengths which on one side or alternatingly on both sides of the primary groove that extend with V-shaped sections which with their legs extend from the primary groove and whose tips point away from the primary groove, alternatingly to this and the other side of the primary groove.

12. The medical instrument according to claim 11, wherein the V-shaped sections have a long leg and a short leg, wherein the short leg is perpendicular to the primary groove and the long leg encloses an acute angle with the primary groove.

13. The medical instrument according to claim 11, wherein the V-shaped sections are uniform and with their acute angle are oriented to the same end of the instrument.

14. The medical instrument according to claim 1, wherein a width of the grooves is less than a few hundreds of a millimeter.

15. The medical instrument according to claim 1, wherein an outer diameter of the outer tube of the instrument is less than 2.5 mm.

16. The medical instrument according to claim 1, wherein the outer tube and the inner tube with the one or more grooves are made from elastic medical stainless steel.

17. The medical instrument according to claim 7, wherein the outer tube and the inner tube are provided with at least one primary groove which is spiral-shaped and runs over equal lengths and with the same pitch in the outer tube and the inner tube both tubes.

18. The medical instrument according to claim 8, wherein the outer tube and the inner tube contain one or more sinus-shaped secondary grooves which extend alternatingly on both sides of a primary groove in overlapping lengths of the outer tube and the inner tube.

19. The medical instrument according to claim 8, wherein at least one secondary groove is a block-shaped groove which extends alternatingly on both sides of a primary groove with sections departing from the primary groove perpendicular to the primary groove and which are connected by sections at a distance from the primary groove in both the outer tube and the inner tube.

20. The medical instrument according to claim 8, wherein the outer tube and the inner tube contain one or more toothed secondary grooves in the overlapping lengths which on one side or alternatingly on both sides of the primary groove that extend with V-shaped sections which with their legs extend from the primary groove and whose tips point away from the primary groove, alternatingly to this and the other side of the primary groove.

* * * * *